(12) United States Patent
Lai et al.

(10) Patent No.: US 10,695,381 B2
(45) Date of Patent: Jun. 30, 2020

(54) TISSUE REPAIR MATERIAL DERIVED FROM FISH SKIN AND MANUFACTURING METHOD THEREOF

(71) Applicant: Body Organ Biomedical Corp., Taipei (TW)

(72) Inventors: Horng-Ji Lai, Taipei (TW); Min-Chang Huang, Taipei (TW); Jui-Min Ho, Taipei (TW); Yun-Ting Hsu, Taipei (TW); Yu-Chi Lin, Taipei (TW); Ta-Wei Su, Taipei (TW); Kuan-Hao Huang, Taipei (TW); Yu-Wei Chang, Taipei (TW)

(73) Assignee: BODY ORGAN BIOMEDICAL CORP., Taipei (TW)

( * ) Notice: Subject to any disclaimer, the term of this patent is extended or adjusted under 35 U.S.C. 154(b) by 0 days.

(21) Appl. No.: 16/179,221

(22) Filed: Nov. 2, 2018

(65) Prior Publication Data
US 2019/0070224 A1 Mar. 7, 2019

Related U.S. Application Data

(62) Division of application No. 15/082,441, filed on Mar. 28, 2016, now Pat. No. 10,172,891.

(60) Provisional application No. 62/140,508, filed on Mar. 31, 2015.

(51) Int. Cl.
*A61K 35/60* (2006.01)
*A61L 27/36* (2006.01)
*A61L 27/52* (2006.01)
*A61L 15/40* (2006.01)

(52) U.S. Cl.
CPC .............. *A61K 35/60* (2013.01); *A61L 15/40* (2013.01); *A61L 27/3604* (2013.01); *A61L 27/3687* (2013.01); *A61L 27/3691* (2013.01); *A61L 27/52* (2013.01); *A61L 2430/16* (2013.01); *A61L 2430/40* (2013.01)

(58) Field of Classification Search
None
See application file for complete search history.

(56) References Cited

FOREIGN PATENT DOCUMENTS

CN 102258144 A * 11/2011

* cited by examiner

*Primary Examiner* — Qiuwen Mi
(74) *Attorney, Agent, or Firm* — WPAT, PC

(57) ABSTRACT

A tissue repair material derived from fish skin and manufacturing method thereof is applied to provide the tissue repair material suitable for use as a patch, a cover, a carrier, a scaffold, an implant or a reagent in various tissues. The tissue repair material has collagens to improve the wounded tissue repair, and has particular characters for desired tissue repair application. Furthermore, so far the factors of the terrestrial animal transmitted disease (caused by virus) do not survive on the tissue repair material derived from fish skin.

9 Claims, 14 Drawing Sheets

TISSUE REPAIR MATERIAL DERIVED FROM FISH SKIN AND MANUFACTURING METHOD THEREOF

CROSS-REFERENCES TO RELATED APPLICATIONS

This application is a Division of application Ser. No. 15/082,441, filed on Mar. 28, 2016 with claiming priority under 35 U.S.C. § 119(a) on U.S. Provisional Patent Application Ser. No. 62/140,508, filed on 2015 Mar. 31, the entire contents of which are hereby incorporated by reference.

BACKGROUND

Technical Field

The instant disclosure relates to a tissue repair material, and particularly relates to a tissue repair material derived from fish skin and manufacturing method thereof, where the tissue repair material is suitable for use as a patch, a cover, a carrier, a scaffold, an implant or a reagent in various tissues.

Related Art

Tissue engineering that involves the incorporation of a biomaterial with biologics and/or pharmaceutics and upon implantation in a patient will stimulate angiogenesis, tissue integration, and/or tissue remodeling. The biomaterial is a tissue repair material which is synthetic and biocompatible and is used to construct artificial organs, rehabilitation devices, or prostheses and replace natural body tissues.

Collagens are important components in tissue repair material, and have the capabilities of improving tissue growing, improving wound healing, and etc. Additionally, the applications of the tissue repair material with collagens continue to expand. Consequently, it is one of topic researches that the tissue repair material with collagens which has higher medical values and wider diversities is developed for various applications.

Nowadays, the tissue repair materials with collagens are autologous or originate from the donor or the animals. However, in certain diseases, the autologous tissue repair materials cannot be acquired or the acquired tissue repair materials are not enough to use. Furthermore, these tissue repair materials originating from the donor has the difficulty in the supply of donor, the complicated preparing procedure, relatively costly, risk of immunological rejection, and etc. And, these tissue repair materials originating from the animals has the complicated preparing procedure, relatively costly, risk of immunological rejection and terrestrial animal transmitted disease.

SUMMARY

In an embodiment, a tissue repair material derived from fish skin includes an optically clear flake derived from a fish skin. The optically clear flake is cell clean and includes a collagen matrix and water in the collagen matrix.

In some embodiments, the optically clear flake has a light transmittance larger than or equal to 70%, an ultimate stress larger than or equal to 5 MPa, and a sewability larger than or equal to 40 g.

In some embodiments, the collagen matrix is a layer structure formed with a plurality of collagen fibers, and each of the plurality of collagen fibers extends along a surface of the optically clear flake. In other embodiments, the collagen matrix is a layer structure formed with a plurality of collagen fibers, and a part of the plurality of collagen fibers extends along a direction from a surface of the optically clear flake to another surface of the optically clear flake.

In some embodiments, the optically clear flake is derived from the fish skin completely without fish scales and a fish flesh.

In some embodiments, the optically clear flake is derived from the fish skin without grinding.

In some embodiments, the optically clear flake is made by a manufacturing method comprising removing fish scales, oil, cells, chromatophores and pocket structures from the fish skin to obtain a purified fish skin, treating the purified fish skin with first acidic solution to obtain a shapeable flake without breakdown, shaping the shapeable fish skin to obtain a shaped flake in a particular form, and performing a stabilization procedure to stabilizing the shaped flake.

In an embodiment, a manufacturing method of a tissue repair material derived from fish skin includes obtaining a fish skin without a fish flesh, removing fish scales, oil, cells, chromatophores and pocket structures from the fish skin to obtain a purified fish skin, and treating the purified fish skin with acidic solution to obtain a shapeable flake without breakdown.

In some embodiments, the manufacturing method further includes washing the shaped fish skin with water. In some embodiments, the shaped flake may be dehydrated before the washing step or after the washing step. In some embodiments, the shaped flake may be backwatered after the dehydrating steps.

In some embodiments, the manufacturing method further includes shaping the shapeable fish skin to obtain a shaped flake in a particular form. In some cases, the shaping step may include cutting the shapeable flake to obtain the shaped flake, and a surface of the shaped flake is a cross section of the shapeable flake. In other cases, the shaping step may include cutting the shapeable flake to obtain the shaped flake, and a surface of the shaped flake is a surface of the shapeable flake.

In some embodiments, the manufacturing method further includes extracting a collagen solution from the shapeable flake.

In some embodiments, the manufacturing method further includes lyophilizing the shapeable flake.

In some embodiments, the manufacturing method further includes removing at least one outer layer of the shapeable flake; and treating the shapeable flake without the at least one outer layer with acidic solution.

In an embodiment, a tissue repair material derived from fish skin made by the aforementioned manufacturing method.

As above, according to the embodiments, the tissue repair material derived from fish skin and manufacturing method thereof is applied to provide the tissue repair material suitable for use as a patch, a cover, a carrier, a scaffold, an implant or a reagent in various tissues. The tissue repair material has collagens to improve the wounded tissue repair, and has particular characters for desired tissue repair application. Furthermore, so far the factors of the terrestrial animal transmitted disease (caused by virus) do not survive on the tissue repair material derived from fish skin.

BRIEF DESCRIPTION OF THE DRAWINGS

The disclosure will become more fully understood from the detailed description given herein accompanying by the following figures, which are illustration only, and thus not limitative of the disclosure, wherein.

DETAILED DESCRIPTION

The ordinal terms, such as first, second, third, etc., mentioned hereafter are applied to distinguish the elements only, but not applied to sequence or to restrict the elements; also they are not applied to limit the scope of the disclosure.

In an embodiment, a tissue repair material derived from fish skin includes an flake derived from a fish skin. The flake is cell clean, and the flake includes a collagen matrix and water in the collagen matrix. The flake derived from a fish skin has sufficient sewability to be applied in various tissue repair application. Herein, the tissue repair material derived from fish skin is suitable for use as a patch, a cover, a carrier, a scaffold, an implant or a reagent in various tissues, such as ocular tissues, oral tissues, the skin, bones, etc. In some embodiments, the flake is an optically clear flake, so as to observe the wound and/or to be suitable to repair the ocular tissues. In some embodiments, the flake also has sufficient ultimate stress to use as a patch, a cover, a carrier, a scaffold, or an implant.

In some embodiments, the optically clear flake has a light transmittance larger than or equal to 70%, and an ultimate stress larger than or equal to 5 MPa. In some embodiments, the optically clear flake has a sewability larger than or equal to 40 g.

In some embodiments, the collagen matrix is a layer structure formed with a plurality of collagen fibers. In some embodiments, each of the plurality of collagen fibers extends along a surface of the optically clear flake. In other embodiments, a part of the plurality of collagen fibers extends along a direction from a surface of the optically clear flake to another surface of the optically clear flake.

Figure 1:
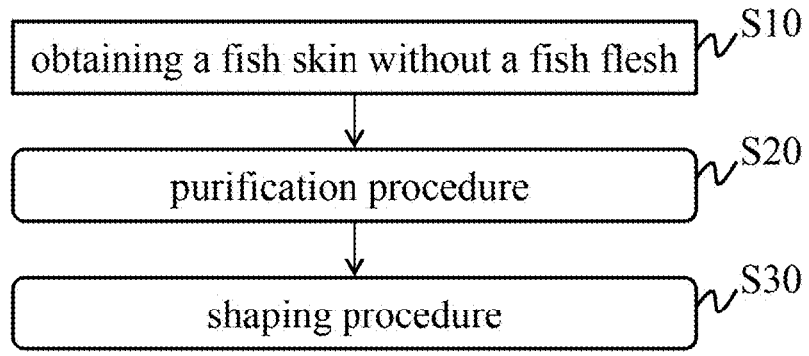
FIG. 1 illustrates a flow chat of an embodiment of a manufacturing method of the tissue repair material derived from fish skin.

Please referring to FIG. 1, in one embodiment, a manufacturing method of the tissue repair material derived from fish skin mainly has a purification procedure (step S20) and a shaping procedure (step S30) after obtaining a fish skin without a fish flesh (step S10).

In some embodiments of the step S10, the fish skin may be an original fish skin with fish scales, but without the fish flesh. In particular embodiment, a fish is obtained from a fish market capable of providing traceability documents or other relevant certified documents, and the fish skin of the obtained fish is separated from the fish flesh thereof to obtain the original fish skin which has fish scales but does not have the fish flesh. In some embodiments, the fish may be a fish whose chromatophores only exist in the surface layer of the fish skin thereof, such as bass, bream, Serranidae fish (e.g., grouper), tilapia, or any combination thereof.

Figure 2:
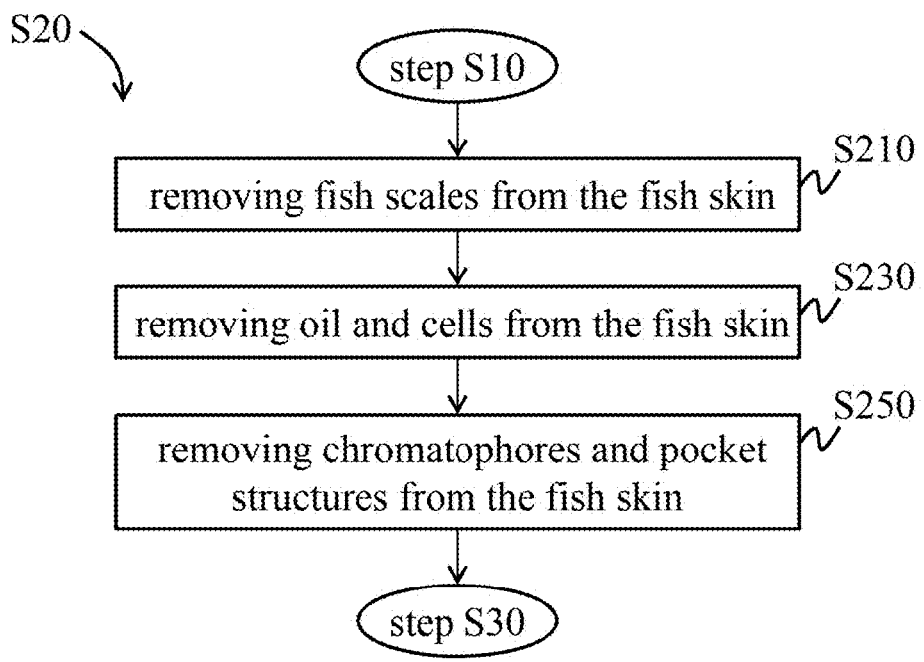
FIG. 2 illustrates a flow chat of an embodiment of step 20.

Please referring to FIG. 2, the purification procedure (step S20) includes removing fish scales from the fish skin (step S210), removing oil and cells from the fish skin (step S230), and removing chromatophores and pocket structures from the fish skin (step S250). The purification procedure (step S20) is completed to obtain a purified fish skin.

In one embodiment of the step S210, the fish scales are removed from the original fish skin completely by using at least one first way to obtain a de-scaled fish skin, and then the de-scaled fish skin is washed by clean water to remove unwanted substances thereon, such as the tissue fluids, bloods, or any combination thereof. In some embodiments, the at least one first way may be at least one physical way, at least one chemical way, or any combination thereof. In the physical way, for example, but not limited thereto, the fish scales are removed by hands, the fish scales are scraped by a planer tool, the fish scales are removed by liquid shear forces, the fish scales are removed by high pressure gas (or liquid), or the original fish skin is immersed in warm water with a temperature of 25 Celsius degrees (° C.) to 60° C. to remove the fish scales. In one embodiment of the chemical way, for example, but not limited thereto, the original fish skin is immersed in an acidic solution to remove the fish scales. In some embodiments, the acidic solution may be an organic acidic solution or an inorganic acidic solution. Herein, the acidic solution may be succinic acid, formic acid, acetic acid, citric acid, pyruvic acid, fumaric acid, hydrochloric acid (HCl), nitric acid ($HNO_3$), or sulfuric acid ($H_2SO_4$). In another embodiment of the chemical way, for example, but not limited thereto, the original fish skin is immersed in a basic solution to remove the fish scales. Herein, the basic solution may be sodium hydroxide (NaOH), or potassium hydroxide (KOH). In yet another embodiment of the chemical way, for example, but not limited thereto, the original fish skin is immersed in hydrogen peroxide ($H_2O_2$) to remove the fish scales.

In one embodiment of the step S230, the oil and the cells are removed from the de-scaled fish skin in the same treatment or in different treatments. Finally, the treated fish skin (i.e. the de-scaled fish skin after removing the oil and the cells) are washed with water to remove unwanted substances on the treated fish skin and/or neutralize the pH value of the treated fish skin. Herein, the water may be clean water, deionized water, double-distilled water (DDW), normal saline, phosphate-buffered saline (PBS), or sodium phosphate buffer (PB). In some embodiments, for removing the oil, the de-scaled fish skin may be treated with at least one chemical agent. Herein, the chemical agent may be an alcoholic solution, a basic solution or any combination thereof. For example, the alcoholic solution may be isopropanol. For example, the basic solution may be NaOH, or KOH. In some embodiments, for removing the cells, the de-scaled fish skin may be treated by using at least one second way. In some embodiments, the at least one second way may be at least one chemical way, at least one enzyme treatment way, at least one physical way, or any combination thereof. In the chemical way, at least one chemical agent is used to remove the cells from the de-scaled fish skin. Herein, the at least one chemical agent may be at least one salt, at least one basic solution, at least one acidic solution, at least one oxidizing agent, at least one chelating agent, or any combination thereof. For example, the salt may be sodium chloride (NaCl), or potassium chloride (KCl). For example, the basic solution may be NaOH, or KOH. For example, the acidic solution may be succinic acid, formic acid, acetic acid, citric acid, pyruvic acid, fumaric acid, HCl, $HNO_3$, or $H_2SO_4$. For example, the oxidizing agent may be hydrogen peroxide, or persulfate ion. For example, the chelating agent may be the agent containing transition metal such as $Ca^{2+}$, $Fe^{2+}$, $Mn^{2+}$, or any combination thereof. In the enzyme treatment way, at least one enzyme is used to remove the cells from the de-scaled fish skin. Herein, the enzyme may be protease, endonuclease, or exonuclease. For example, the endonuclease may be EcoRI, BamHI, HindIII, TaqI, NotI, HinfI, or Sau3A. For example, the exonuclease may be ribonuclease R, ribonuclease II, ribonuclease D, RNase BN, ribonuclease PH, or exonuclease I. In some embodiments of the physical way, the de-scaled fish skin is frozen to remove the cells from the de-scaled fish skin. In an example of the step S230, the de-scaled fish skin is immersed in a mixture solution of NaOH and NaCl for 12 to 24 hours, and the mixture solution is renewed for several times during the immersion, to obtain the treated fish skin. After the immersion, the treated fish skin is washed with the DDW to wash off the mixture solution until the pH value of the fish skin is neutral. In some embodiments, during the step S230, the treatment temperature may be controlled in 4° C. to 20° C. For example, in the step S230, all used solutions have the temperature of 4° C. to 20° C., and/or the ambient temperature is controlled in 4° C. to 20° C.

In one embodiment of the step S250, the chromatophores and the pocket structures are removed from the treated fish skin (neutral) in the same treatment or in different treatments. In an embodiment, the treated fish skin is immersed in at least one acidic solution, so that the treated fish skin is swelling (hereafter referred to as swelling fish skin). Then, the swelling fish skin is applied with a pocket-removing way, to remove the pocket structures. Herein, the acidic solution may be, for example, but not limited thereto, succinic acid, formic acid, acetic acid, citric acid, pyruvic acid, fumaric acid, HCl, $HNO_3$, or $H_2SO_4$. The different concentrations of the acidic solutions are taken according to the different kinds of the acidic solutions. Also, the different immersion times are taken according to the different concentrations of the acidic solutions. For example, when 0.01 M to 0.5 M acetic acid is used, the immersion time is 0.5 hours to 18 hours; or when 0.3 M acetic acid is used, the immersion time is about 30 minutes to 50 minutes. Moreover, the parameters (i.e. concentrations and immersion times) are also adjusted according to the size of the treated fish skin. In one case, the chromatophores are also removed from the swelling fish skin during the pocket-removing way is carried out. In another case, the swelling fish skin is further treated with at least one chromatophore-removing agent. In some embodiments of the pocket-removing way, a blunt tool is used to remove the pocket structures. For example, the blunt tool may be the hands, an iron sheet, a plastic sheet, or other tool which do not damage the surface of the fish skin. In some embodiments, the chromatophore-removing agent may be oxidizing agent (e.g., hydrogen peroxide, sodium hypochlorite) or surfactant (e.g., Triton X100). In some embodiments, the surface grain, the muscle tissues and the unnecessary residual tissues are also removed from the swelling fish skin during the pocket-removing way is carried out.

It should be understood that the sequence of performing the step S210, the step S230 and the step S250 is not limited to the above described explanation. The implementation sequence may be adjusted according to the content of each step, or two or all of the step S210, the step S230 and the step S250 are combined into one step according to the content of each step. For example, the fish skin is immersed in the acidic solution to be swelling, and then the fish skin the pocket structures are removed from the swelling fish skin by using the blunt tool.

Figure 3:
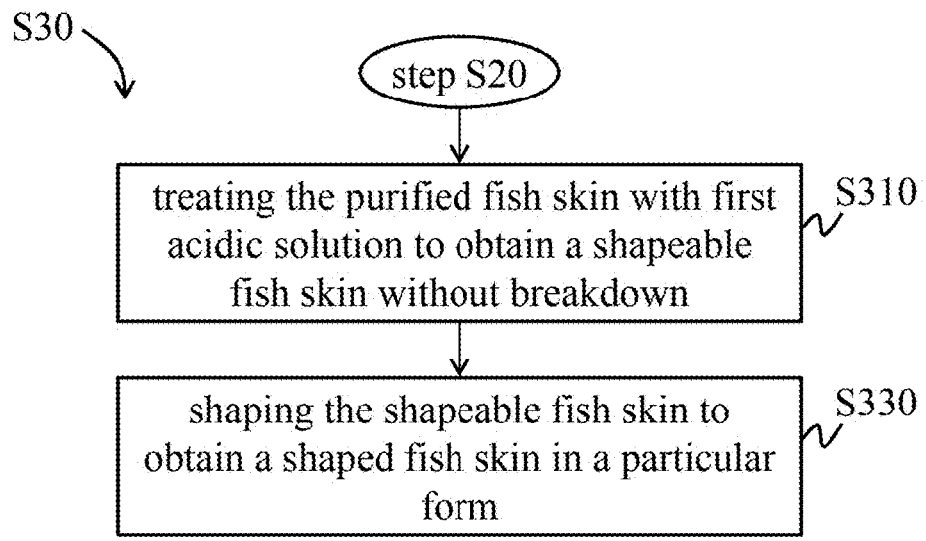
FIG. 3 illustrates a flow chat of an embodiment of step 30.

Please referring to FIG. 3, the shaping procedure (step S30) includes treating the purified fish skin with an acidic solution to obtain a shapeable flake derived from the fish skin without breakdown (step S310), and shaping the shapeable flake into a particular form to obtain a shaped flake derived from the fish skin in a particular form (step S330). Herein, the shaped flake may be optically clear.

In some embodiments of the step S310, the purified fish skin is immersed in at least one acidic solution, so that the purified fish skin is swelling but without breakdown (i.e. the shapeable flake derived from the fish skin). Then, the shapeable flake is shaped in a particular form by using a tool or a mold, to form the shaped flake (i.e. the shapeable flake in the particular form). Herein, the acidic solution may be, for example, but not limited thereto, succinic acid, formic acid, acetic acid, citric acid, pyruvic acid, fumaric acid, HCl, $HNO_3$, or $H_2SO_4$. The different concentrations of the acidic solutions are taken according to the different kinds of the acidic solutions. Also, the different immersion times are taken according to the different concentrations of the acidic solutions. In some embodiments, the particular form of the shaped flake may be sheet, pocket with planar surface, convex, tubular, linear or nonlinear bar (e.g., single line, or a plurality of lines strung), ball (e.g., powder, or fine particle), bulk, needle, solid polyhedron or hollowed polyhedron.

In some embodiments, during the shaping step (step S330), the shapeable flake may be cut into a particular size. In one case, after cutting, the surface of the shaped flake originates from the surface of the shapeable flake. In another case, after cutting, the surface of the shaped flake originates from the cross-section of the shapeable flake.

In some embodiments, during the shaping step (step S330), there is no grinding the shapeable flake.

Figure 4:
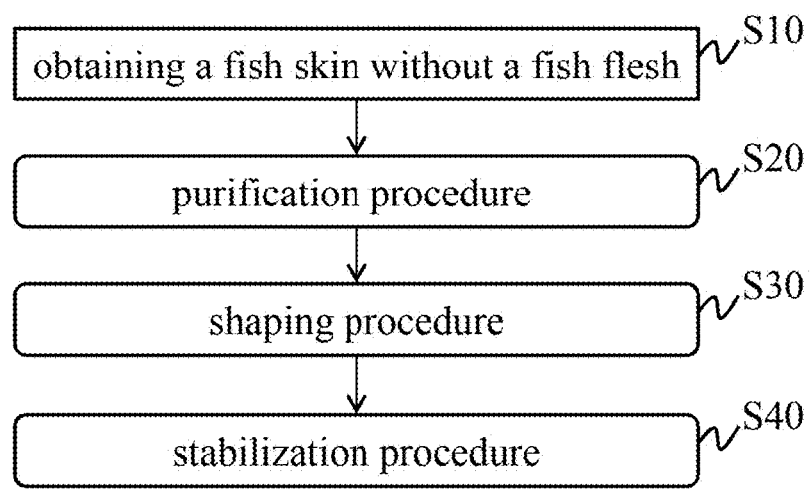
FIG. 4 illustrates a flow chat of another embodiment of the manufacturing method of the tissue repair material derived from fish skin.

In another embodiment, referring to FIG. 4, a stabilization procedure (step S40) is performed after the shaping procedure (step S30).

In one embodiment, the stabilization procedure (step S40) includes stabilizing the shaped flake to obtain the optically clear flake in stable state.

Figure 5:
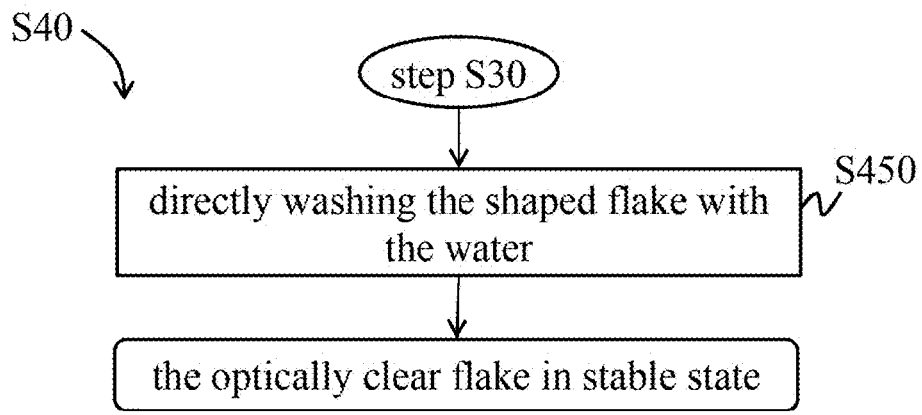
FIG. 5 illustrates a flow chat of first embodiment of step 40.

In a first embodiment of the stabilizing step, referring to FIG. 5, after the shaping procedure (step S30), the shapeable flake is directly washed with water until the pH value of the flake is neutral (step S450). That is, there is no any dehydrating step between the shaping procedure (step S30) and the washing step (step S450).

Figure 6:
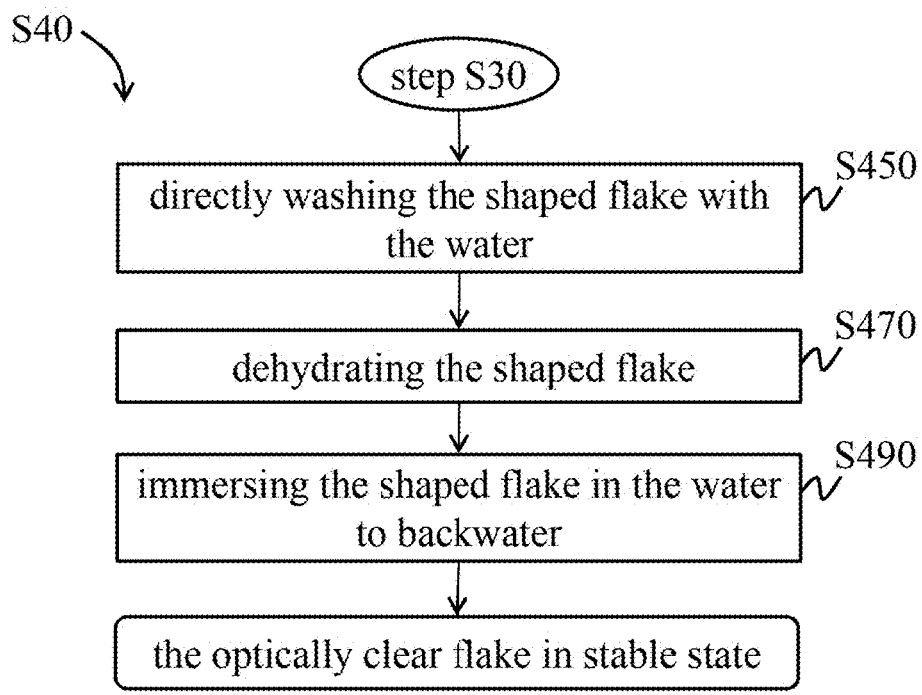
FIG. 6 illustrates a flow chat of second embodiment of step 40.

In a second embodiment of the stabilizing step, referring to FIG. 6, after the shaping procedure (step S30), the shapeable flake is directly washed with water until the pH value of the flake is neutral to obtain a neutral flake derived from fish skin (step S450). After the washing step, the neutral flake is dehydrated (step S470), and then immersed in the water to backwater (step S490).

Figure 7:
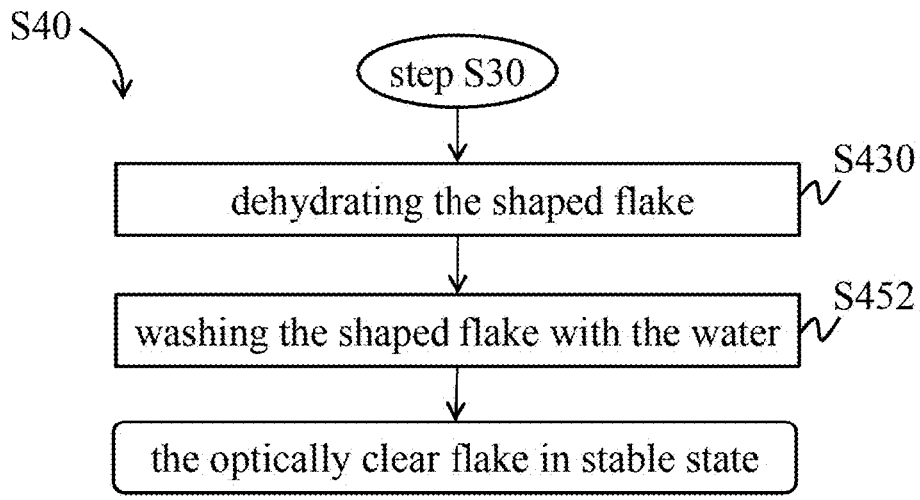
FIG. 7 illustrates a flow chat of third embodiment of step 40.

In a third embodiment of the stabilizing step, referring to FIG. 7, after the shaping procedure (step S30), the shaped flake is dehydrated (step S430), and then washed with water until the pH value of the flake is neutral to obtain the neutral flake derived from fish skin (step S452).

Figure 8:
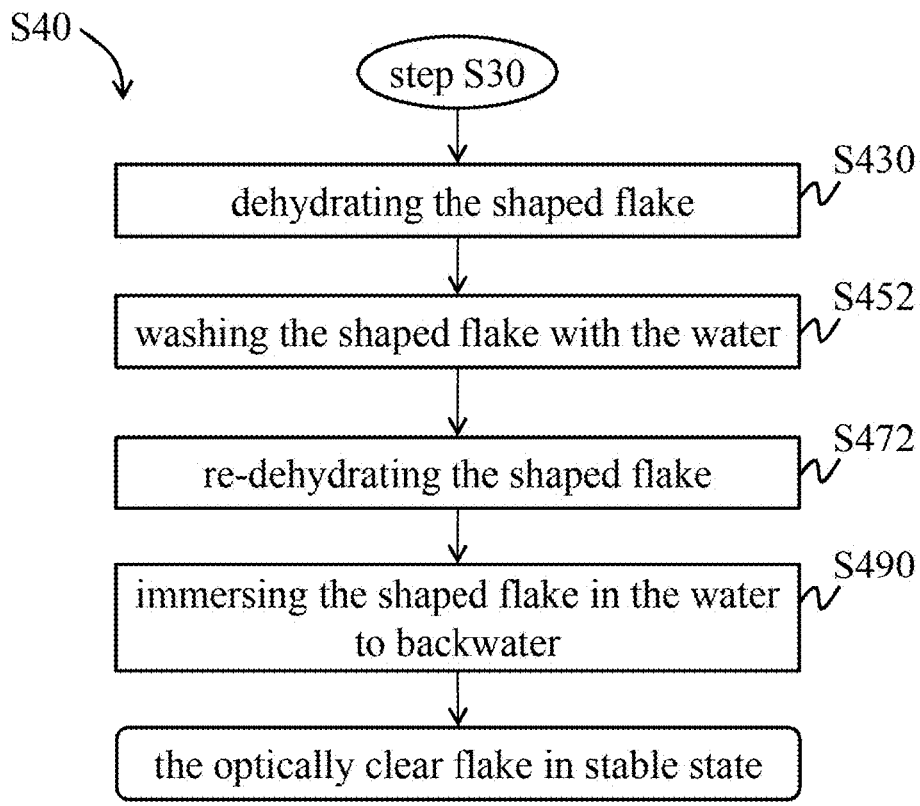
FIG. 8 illustrates a flow chat of fourth embodiment of step 40.
Figure 9:
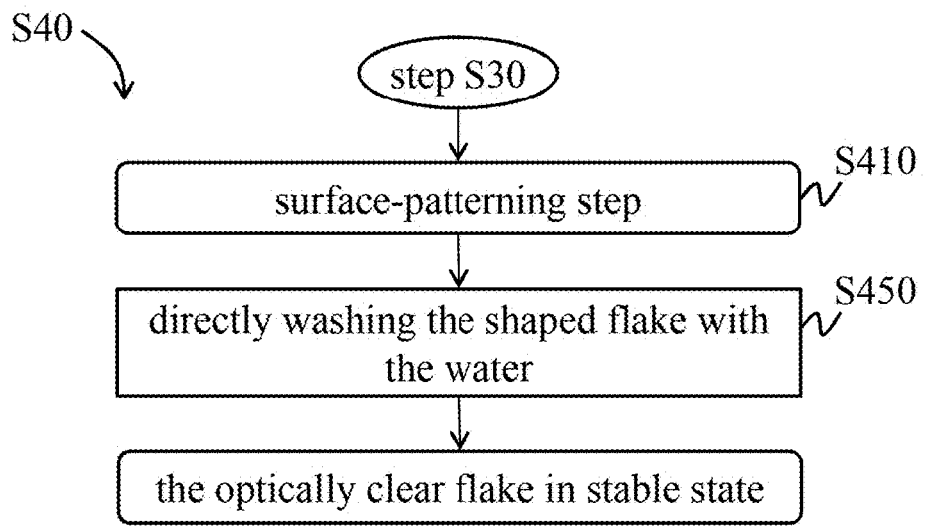
FIG. 9 illustrates a flow chat of fifth embodiment of step 40.
Figure 10:
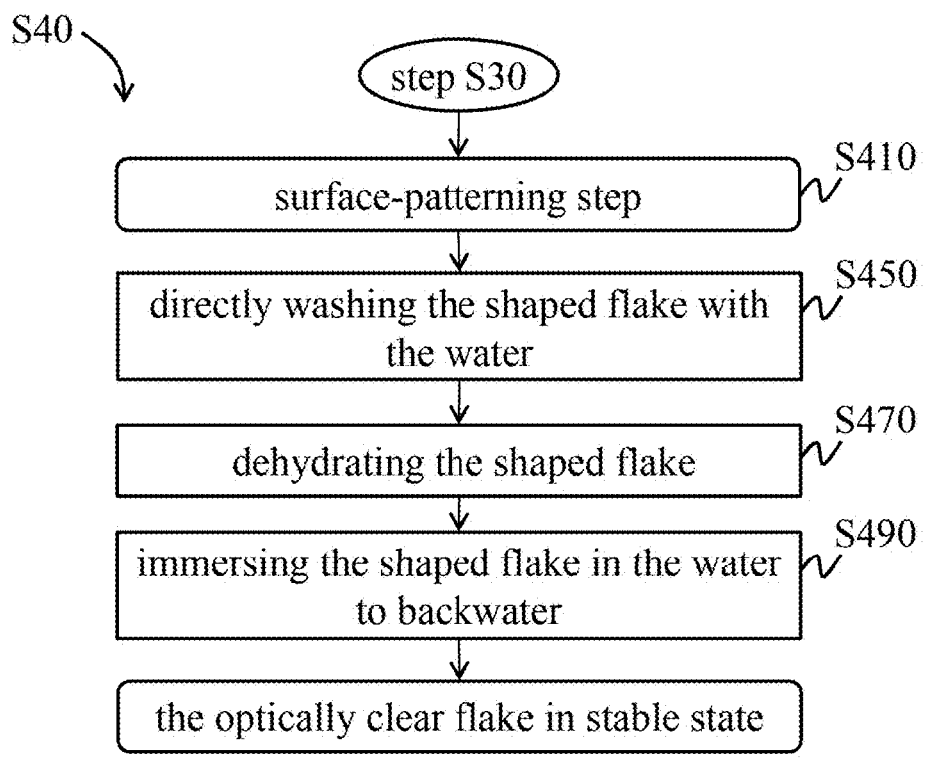
FIG. 10 illustrates a flow chat of sixth embodiment of step 40.
Figure 11:
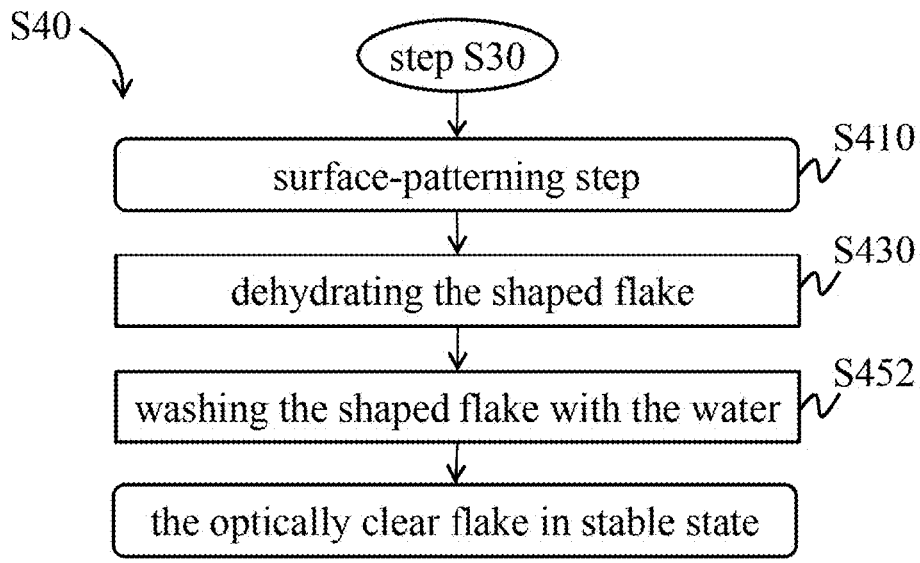
FIG. 11 illustrates a flow chat of seventh embodiment of step 40.
Figure 12:
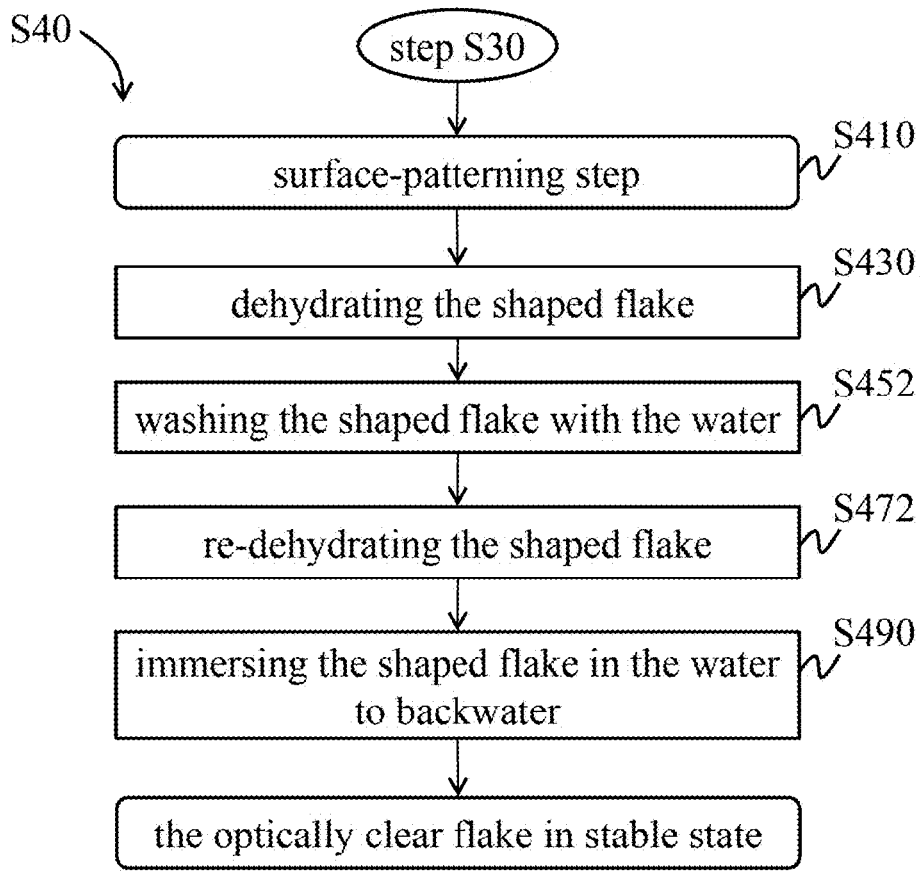
FIG. 12 illustrates a flow chat of eighth embodiment of step 40.

In a fourth embodiment of the stabilizing step, referring to FIG. 8, after the shaping procedure (step S30), the shaped flake is dehydrated (step S430), and then washed with water until the pH value of the flake is neutral to obtain the neutral flake derived from fish skin (step S452). After the washing step, the neutral flake is re-dehydrated (step S472), and then immersed in the water to backwater (step S490).

In the stabilization procedure (step S40), the used water may be clean water, deionized water, DDW, normal saline, PBS, or PB. In the stabilization procedure (step S40), the dehydrating way is gentle, such as air-dehydrating, or low temperature dehydrating.

In another embodiment, referring to FIGS. 9 to 12, during the stabilization procedure (step S40), a surface-patterning step (step S410) is performing before the stabilizing step.

In one embodiment of the surface-patterning step (step S410), the shaped flake is placed in a mold having specific pattern, so that the surface of the shaped flake has grain. The surface grain of the shaped flake and the specific pattern on the inner surface of the mold are mated with each other. Herein, the surface grain may be, for example, but not limited thereto, a protruded grain, a recessed grain, or combination thereof. In other words, the specific pattern on the inner surface of the mold may be, for example, but not limited thereto, a recessed pattern, a protruded pattern, or combination thereof.

In some embodiments, the surface-patterning step (step S410) can be combined into the shaping step (step S330). That is, the surface grain can be formed in the shaping step (step S330), and there is no surface-patterning step (step S410) during the stabilization procedure (step S40).

In some embodiments, the shaping procedure (step S30) and the stabilization procedure (step S40) may be alternately performed once or several times (not shown).

Figure 13:
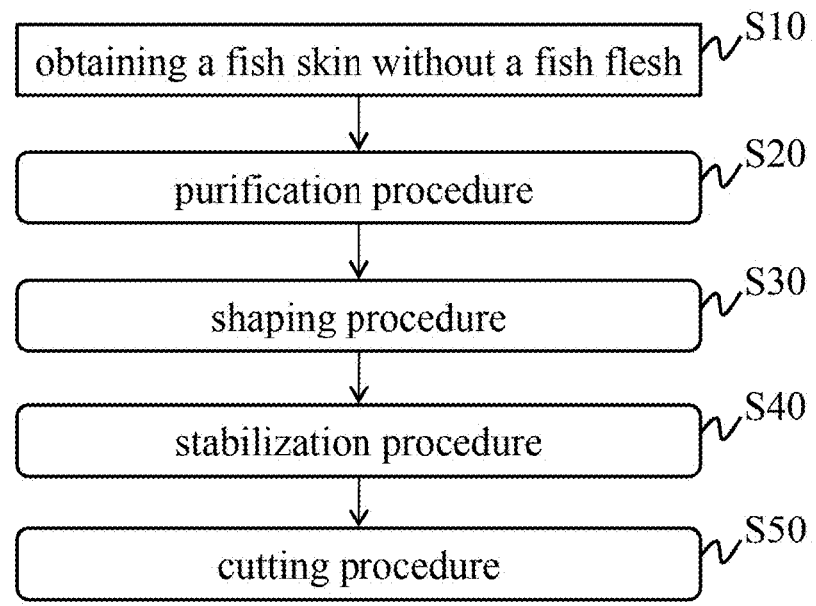
FIG. 13 illustrates a flow chat of yet another embodiment of the manufacturing method of the tissue repair material derived from fish skin.

In yet another embodiment, referring to FIG. 13, a cutting procedure (step S50) is performed after the stabilization procedure (step S40). During the cutting procedure (step S50), the optically clear flake in the stable state is cut into a specific size.

In some embodiments (no shown in FIGs.), a crosslinking procedure is performed between the purification procedure (step S20) and the shaping procedure (step S30), between the shaping procedure (step S30) and the stabilization procedure (step S40), together with the shaping procedure (step S30), or together with the stabilization procedure (step S40). During the crosslinking procedure, the purified fish skin or the optically clear flake are treated by using at least one crosslinking way, to further improve the mechanical properties. In some embodiments, the crosslinking way may be physical crosslinking way or chemical crosslinking way. For example, the physical crosslinking way may be UV, γ-ray or heat. For example, the chemical crosslinking way may be glutaraldehyde (GA), 1,4-butanediol diglycidyl ether (BDDE), genipin, or 1-Ethyl-3-(3-dimethylaminopropyl)-carbodiimide/N-hydroxysuccinimide (EDC/NHS).

In modified embodiments, the shaping procedure (S30) may be modified, and the procedure after the shaping procedure (S30) may be removed. Herein, the shaping procedure may include treating the purified fish skin with the acidic solution to obtain a shapeable flake derived from the fish skin; and extracting a collagen solution from the shapeable flake. Herein, the tissue repair material derived from fish skin is the collagen solution. In some cases, the shaping step (step S330) may be removed. In other cases, the shaping step (step S330) may retain to cut the shapeable flake into a particular size and/or form suitable for extracting.

Furthermore, a neutralizing step may be performed between the acid-treating step and the extracting step, to neutralize the pH value of the shapeable flake to be neutral. The neutralizing step may include, for example, washing the shapeable flake with the water.

In other modified embodiments, the shaping procedure (S30) may be modified, and the procedure after the shaping procedure (S30) may be removed. Herein, the shaping procedure may include treating the purified fish skin with the acidic solution to obtain a shapeable flake derived from the fish skin without breakdown (step S310); and lyophilizing the shapeable flake to obtain a collagen sponge. Herein, the tissue repair material derived from fish skin is the collagen sponge. In some cases, the shaping step (step S330) may be removed. In other cases, the shaping step (step S330) may retain between the acid-treating step (step S310) and the lyophilizing step.

Furthermore, a neutralizing step may be performed between the acid-treating step (step S310) (or the shaping step (step S330)) and the lyophilizing step, to neutralize the pH value of the shapeable flake (or the shaped flake) to be neutral. The neutralizing step may include, for example, washing the flake with the water.

In yet other modified embodiments, the shaping procedure (S30) may be modified. Herein, during the shaping procedure, the acid-treating step (step S310) may be performed more times. And, at least one outer layer of the shapeable flake is removed between the two acid-treating steps (step S310). Finally, the tissue repair material derived from fish skin being the collagen film is obtained. Herein, the parameter of acid-treatment for any two acid-treating steps (step S310) may be the same, or be different.

In some cases, the shaping step (step S330) may be removed. In other cases, the shaping step (step S330) may retain after any acid-treating step (step S310).

In some cases, the procedure after the shaping procedure (S30) may be removed. In other cases, the procedure after the shaping procedure (S30) may retain. If the procedure after the shaping procedure (S30) is removed, a neutralizing step may be performed after the acid-treating step (step S310), to neutralize the pH value of the flake (or the collagen film) to be neutral. The neutralizing step may include, for example, washing the shapeable flake with the water.

First Preparation Procedure: SEM Sample Preparation

A sample (i.e. the fish skin to be observed or the flake to be observed) is placed in the deionized water for 30 minutes. Then, the deionized water is replaced by 2.5% glutaraldehyde solution, and the sample is immersed in the glutaraldehyde solution for 20 minutes. After the immersion of the glutaraldehyde solution, the sample is washed by deionized water three times for 10 minutes per time. Next, the osmic acid is added to react with the sample for 2 hours. Then, the osmic acid is removed, and the sample is washed by the deionized water three times for 10 minutes per time. Next, the alcohols with gradient concentrations (30%, 50%, 70%, 80%, 90%, 95%, and 100%) are applied to dehydrate the sample. Then, the sample is dehydrated in a critical point dryer (EM CPD300, Leica) to obtain the sample for SEM measurement by a scanning electronic microscope (S-3000 N, Hitachi).

Second Preparation Procedure: Frozen Sectioning and H&E Stain

A sample (i.e. the flake to be observed) is immobilized by 4% paraformaldehyde for 24 hours, followed dehydrated in 30% sucrose solution at 4° C. to prevent the formation of ice crystals which may damage the tissues of the sample. The dehydrated sample is then placed to a mold in which an embedding agent (O.C.T) is already added, and the mold is frozen by liquid nitrogen, to form an embedded sample. After the O.C.T is set, the embedded sample is sectioned by a frozen sectioning machine (CM1900, Leica) at −25° C., and the section thickness is 10 µm, to obtain a section sample. The section sample is stained by hematoxyline solution and stored in room temperature for 1 minute. Then the section sample is washed by deionized water and immersed in the deionized water for 10 minutes. Next, the section sample is further stained by eoxin solution for 6 minutes, and then washed by deionized water for 8 minutes. Then, the stained section sample is sequentially dehydrated by the alcohols with gradient concentrations (75%, 85%, 95%, and 100%) and air-dehydrated. After the dehydration, the stained section sample is mounted and observed in an optical microscope (DM6000B, Leica).

First Test Procedure: Mechanical Test

A sample (i.e. the flake to be tested) is cut as dumbbell shaped pieces based on ASTM D638-2003 regulations and fixed on a fixture of a universal testing machine (3365, INSTRON). The mechanical test is performed by the universal testing machine with the speed of 5 mm/min and the force of 500 N. The number of samples is larger than or equal to 6, and the average ultimate stress of the samples is calculated.

Second Test Procedure: Light Transmittance Test

A sample (i.e. the flake to be tested) is immersed in the DDW for 16 hours to backwater. Herein, 8 pieces of the sample is immersed in 500 ml DDW. The sample is cut into a small disk with 0.7 cm diameter, and each small disk is placed in one well of the multiwell dish together with the 100 µl DDW. The absorbance of the small disk is measured by an ELISA meter (Sunrise, TECAN) from 400 nm to 700 nm. The control well is only added the 100 µl DDW. The average absorbance of the absorbance for 400 nm to 700 nm is calculated. The light transmittance is calculated according to the following formula:

$$A = \log 1/T$$

T represents the light transmittance, and A represents the average of the measured absorbance of the small disk.

Third Test Procedure: Thickness Test

The thickness of a sample (i.e. the flake to be tested) is measured by a film thickness meter at a plurality of random and different positions, and the average thickness of the thickness at the random and different positions is calculated, to obtain the tested thickness of the sample.

Fourth Test Procedure: Sewability Test

A sample (i.e. the flake to be tested) is cut into 1*1 cm size. The cut sample is threaded though the position at 0.2 cm from the upper and lower borders thereof by non-absorbable sutures (STIN-ST4 4.0). The upper suture threading through the upper border is fixed in a sewability test stage, and a heavy object is suspend from the lower threading through the lower border. The weight of the heavy object when the cut sample breaks is the sewability of the sample.

Fifth Test Procedure: Water Content Test

A dehydrated sample (i.e. the flake to be tested) is obtained and weighed to record its original weight. Then, the dehydrated sample is twice heated by a drying oven at 105±3° C. until the weight variation is less than 0.05% original weight. After heating, the heated sample is weighed to record its heated weight. The water content is calculated according to the following formula: the water content=[(the original weight−the heated weight)/the original weight]× 100%.

First Experiment: The Observation of the Original Fish Skin

Figure 14:
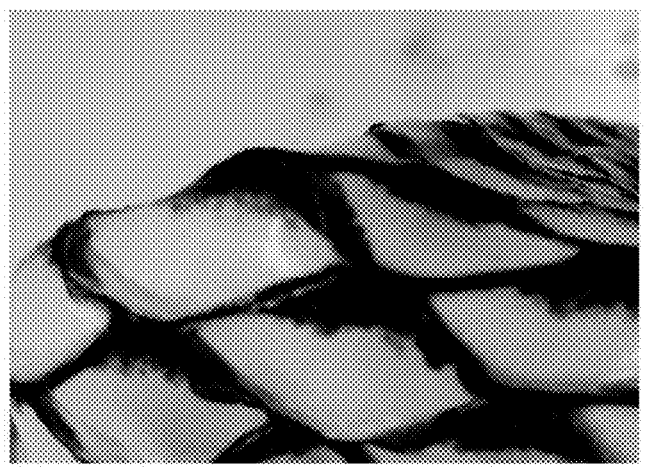
FIG. 14 is a picture showing the surface of the original fish skin.

In macroscopic view, the original fish skin with fish scales is white and opaque, and the original fish skin has a great amount of chromatophores in the pocket structure, as shown in FIG. 14.

The original fish skin with fish scales is treated into the sample for SEM measurement by the first preparation procedure.

Figure 15:
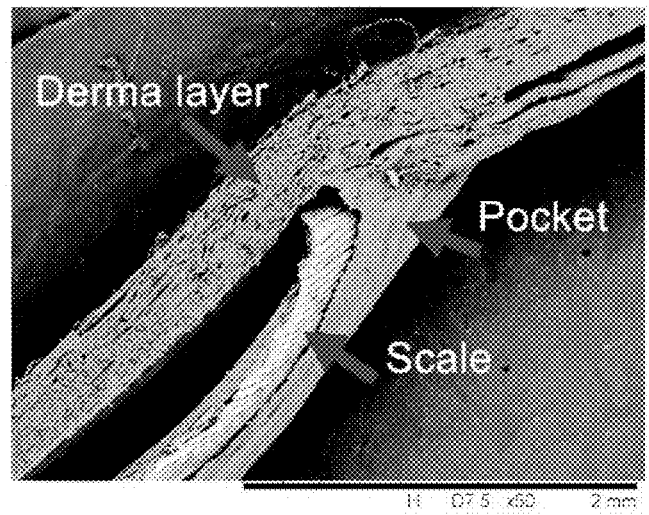
FIGS. 15 to 17 are SEM micrographs of the original fish skin.
Figure 16:
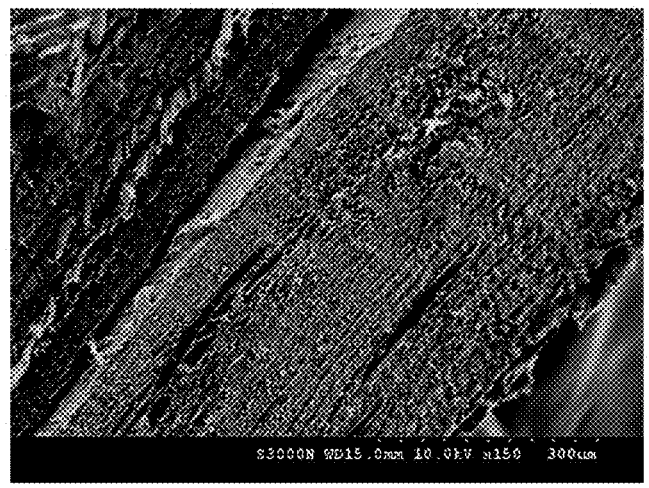
Figure 17:
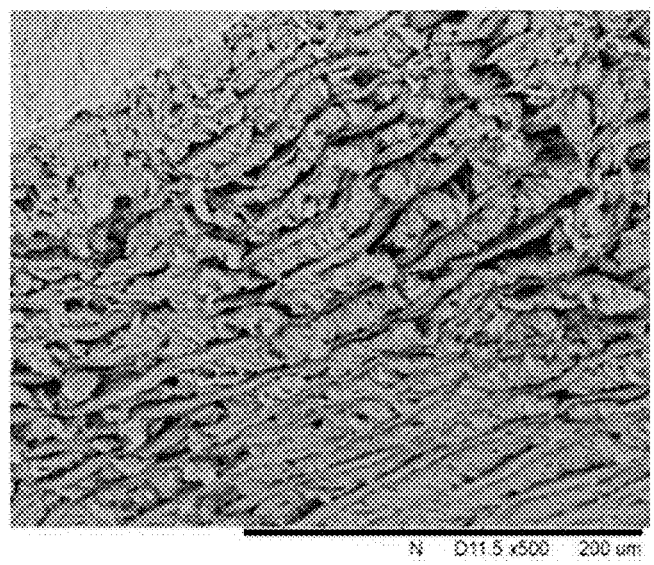

The cross-section of the original fish skin is shown in FIG. 15, where the surface of the original fish skin has protruded connective tissues like pocket to cover the fish scale. Besides the pocket structure, the cross-section of the original fish skin at higher magnification is shown in FIGS. 16 and 17, where the original fish skin has a layer structure.

Second Experiment: The Purification Procedure

After the original fish skin (stored in a low temperature state less than 4° C.) is obtained, the fish scales are completely removed from the original fish skin by manual means to obtain the de-scaled fish skin, and the de-scaled fish skin is washed with clean water to remove the tissue fluids and bloods to obtain the clean de-scaled fish skin. The clean de-scaled fish skin is immersed in a mixture solution having 0.5 M NaOH and 0.5 M NaCl for 12 hours, so that the fish skin swells and becomes opaque (called as the treated fish skin). Then, the treated fish skin is washed with the equal-volume water by stirring the water, and the water is renewed once or repeatedly to repeatedly washing the fish skin until the mixture solution is removed (i.e., until the color of the fish skin turns into white, and the pH value is neutral). The treated fish skin (neutral) is immersed in 1 L/0.3 M acetic acid solution for 60 minutes. After the immersion of the acetic acid solution, the pocket structures on the surface of the treated fish skin becomes fragile, and the pocket structures can be completely removed by a finger, to obtain the purified fish skin (hereafter referred to as first purified fish skin).

Third Experiment: The Purification Procedure

After the original fish skin (stored in a low temperature state less than 4° C.) is obtained, the fish scales are completely removed from the original fish skin by manual means to obtain the de-scaled fish skin, and the de-scaled fish skin is washed with clean water to remove the tissue fluids and bloods to obtain the clean de-scaled fish skin. The clean de-scaled fish skin is immersed in a mixture solution having 0.1 M NaOH and 10% NaCl for 12 hours, so that the fish skin swells and becomes opaque (called as the treated fish skin). Then, the treated fish skin is washed with the equal-volume water by stirring the water, and the water is renewed once or repeatedly to repeatedly washing the fish skin until the mixture solution is removed (i.e., until the color of the fish skin turns into white, and the pH value is neutral). The treated fish skin (neutral) is immersed in 0.1 M acetic acid solution for 30 minutes. After the immersion of the acetic acid solution, the pocket structures on the surface of the treated fish skin becomes fragile, and the pocket structures can be completely removed by the blunt tool, to obtain the purified fish skin (hereafter referred to as second purified fish skin).

Fourth Experiment: The Observation of the Second Purified Fish Skin

The second purified fish skin is treated into the sample for SEM measurement by the first preparation procedure.

Figure 18:
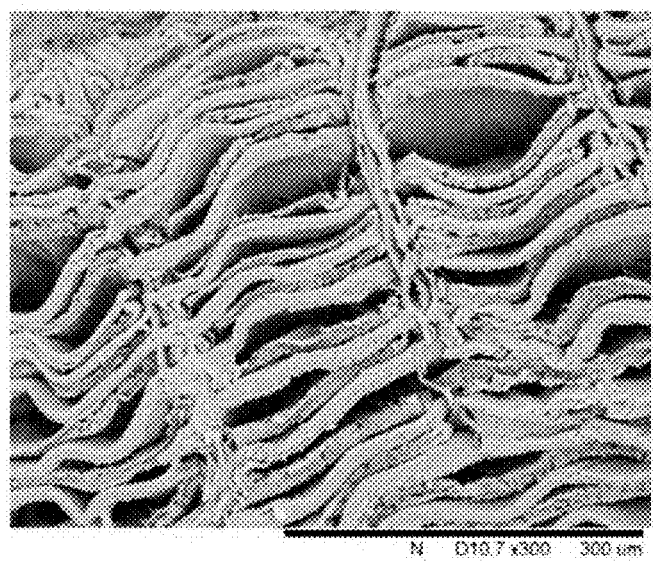
FIG. 18 is SEM micrograph of the second purified fish skin.

The cross-section of the second purified fish skin has a collagen matrix, and the collagen matrix is a layer structure formed with a plurality of collagen fibers, as shown in FIG. 18. Referring to FIG. 18, the collagen fibers are loosely arranged into a plurality of layers of the layer structure, the collagen fibers in the same layer are arranged in the same direction, and the collagen fibers in two adjacent layers crisscross at 90-degree angle horizontally. Besides, there are the longitudinal fibers vertical to those horizontal layers.

Fifth Experiment: The Shaping Procedure, the Stabilization Procedure and the Crosslinking Procedure The first purified fish skin is immersed in a 0.5 L/0.3 M acetic acid solution for 24 hours, so that the first purified fish skin becomes in a shapeable-state (hereafter referred to as first shapeable flake) in which the thickness and the shape can be controlled easily.

The first shapeable flake is placed in a mold with a smooth surface to obtain the shaped flake, and then the shaped flake is placed in a fume hood together with the mold until the shaped flake is completely dehydrated. After the dehydration, the shaped flake is immersed in 1 L water by stirring the water until the solution is washed off. Next, the shaped flake is placed in the mold again, and then is completely dehydrated again. Accordingly, the optically clear flake in stable state is obtained (hereafter referred to as first stable flake).

In one case, the first stable flake is placed at a position 50 cm away from the UV light (110 V, 8 W, and 254 nm). Each surface of the first stable flake is illuminated by the UV light for 60 minutes twice per surface, to the optically clear flake in stable state (hereafter referred to as second stable flake).

In another case, the first stable flake is placed in a 1% BDDE (or 0.05% GA) solution for 12 hours along with stirring the BDDE solution. Next, the first stable flake is washed by the deionized water three times for 10 minutes per time, to the optically clear flake in stable state (hereafter referred to as third stable flake).

Sixth Experiment: The Observation of the First Shapeable Flake

Figure 19:
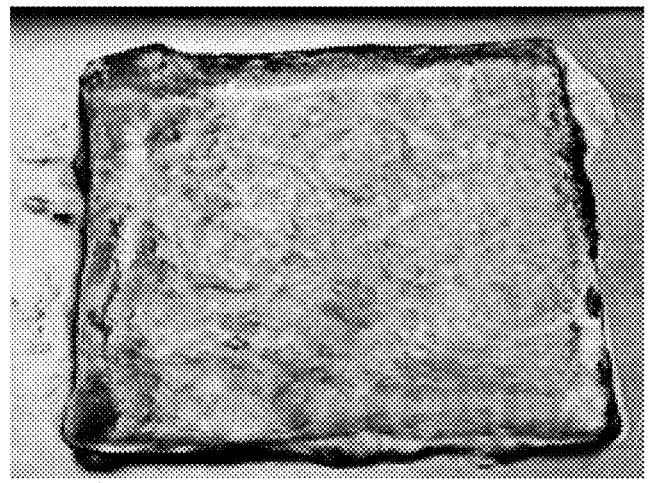
FIG. 19 is a picture showing the first shapeable flake.

In macroscopic view, the first shapeable flake is transparent and like a water gel, as shown in FIG. 19.

Figure 20:
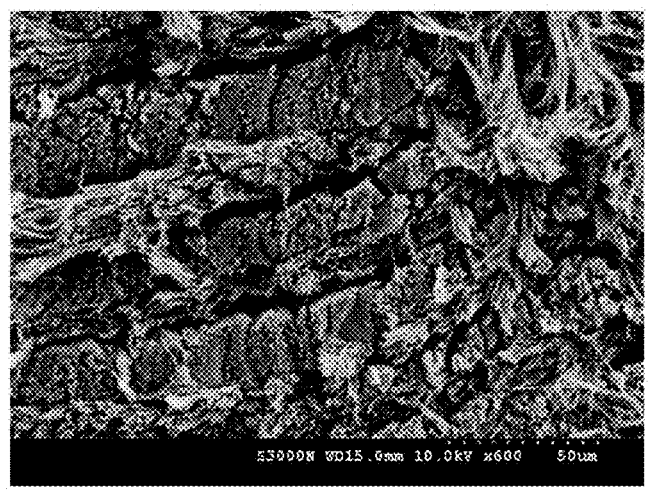
FIG. 20 is SEM micrograph of the first shapeable flake.

The first shapeable flake is treated into the sample for SEM measurement by the first preparation procedure. Under SEM measurement, the cross-section of the first shapeable flake is shown in FIG. 20, where the layer structure of the first shapeable flake is loose.

Figure 21:
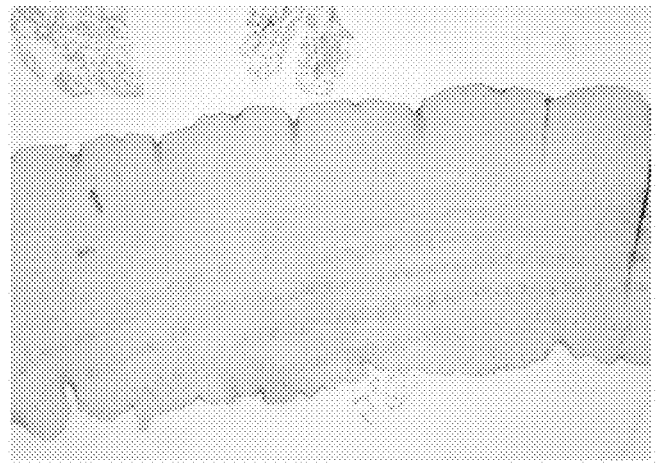
FIG. 21 is a micrograph of the stained section sample of the first shapeable flake.

The first shapeable flake is treated into the stained section sample by the second preparation procedure. The stained section sample of the first shapeable flake is observed that the first shapeable flake does not remain any cell, as shown in FIG. 21.

Seventh Experiment: The Observation of the First to Third Stable Flakes

Figure 22:
FIG. 22 is a picture showing the first stable flake.

In macroscopic view, the first stable flake is transparent and smooth, as shown in FIG. 22.

Figure 23:
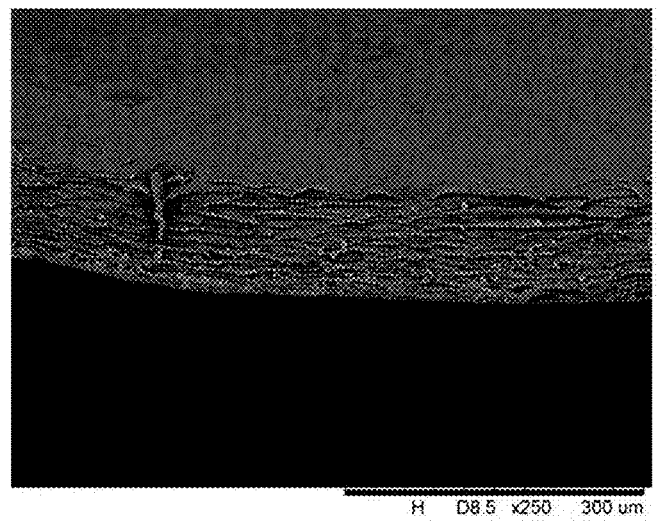
FIGS. 23 and 24 are SEM micrographs of the first stable flake.
Figure 24:
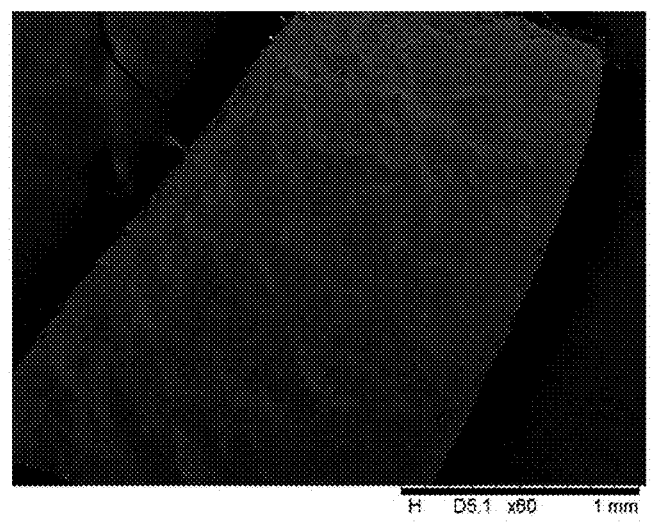

The first stable flake is treated into the sample for SEM measurement by the first preparation procedure. Under SEM measurement, the cross-section of the first stable flake is shown in FIGS. 23 and 24, where the structure of the first stable flake is dense and the surface of the first stable flake is very smooth.

The average ultimate stresses of the first to third stable flakes are shown in the following table 1.

TABLE 1

| | average ultimate stresses (MPa) |
|---|---|
| normal human cornea | 6.499 ± 0.576 |
| first shapeable flake | 5-10 |
| second stable flake | 5-8 |
| third stable flake | 5-25 |

The average ultimate stresses of the first to third stable flakes are close to or larger than that of the normal human cornea.

Eighth Experiment: The Shaping Procedure

The second purified fish skin(s) is(/are) cut into small disks with 16 mm diameter, the small disks divide into 40 groups. The 40 groups of the small disks are immersed in the acetic acid solution in the different reaction conditions as shown in the following table 2.

TABLE 2

| | | The concentration of the acetic acid solution | | | | |
|---|---|---|---|---|---|---|
| group | | 0.01M | 0.05M | 0.1M | 0.3M | 0.5M |
| The immersion time | 5 minutes | 1 | 2 | 3 | 4 | 5 |
| | 15 minutes | 6 | 7 | 8 | 9 | 10 |
| | 0.5 hours | 11 | 12 | 13 | 14 | 15 |
| | 1 hour | 16 | 17 | 18 | 19 | 20 |
| | 2 hours | 21 | 22 | 23 | 24 | 25 |
| | 4 hours | 26 | 27 | 28 | 29 | 30 |
| | 8 hours | 31 | 32 | 33 | 34 | 35 |
| | 24 hours | 36 | 37 | 38 | 39 | 40 |

After the immersion, the second purified fish skins in the 30th and 33th to 40th groups have been breakdown, i.e. their forms cannot maintain.

Ninth Experiment: The Shaping Procedure and the Stabilization Procedure

The second purified fish skin is cut off the fish back portion, the fish belly portion and the fish tail portion where have less collagen and cannot swell better, to retain central rectangular portion of the second purified fish skin. The size of the central rectangular portion is 7*24 cm. The central rectangular portion is re-cut into 8 pieces with the size of 7*3 cm. Herein, the surface of each piece originates from the surface of the central rectangular portion. Each piece is immersed in a 0.5 L/0.1 M acetic acid solution for 6 hours, and then placed into the ice for 16 hours. Next, each piece is laminated in the flakes (hereafter referred to as second shapeable flake).

The second shapeable flake is treated according to the foregoing first embodiment of the stabilizing step, to obtain the optically clear flake in stable state (hereafter referred to as fourth stable flake). The second shapeable flake is treated according to the foregoing second embodiment of the stabilizing step, to obtain the optically clear flake in stable state (hereafter referred to as fifth stable flake). The second shapeable flake is treated according to the foregoing third embodiment of the stabilizing step, to obtain the optically clear flake in stable state (hereafter referred to as sixth stable flake). The second shapeable flake is treated according to the foregoing fourth embodiment of the stabilizing step, to obtain the optically clear flake in stable state (hereafter referred to as seventh stable flake).

Tenth Experiment: The Observation of the Fourth to Seventh Stable Flakes

Figure 25:
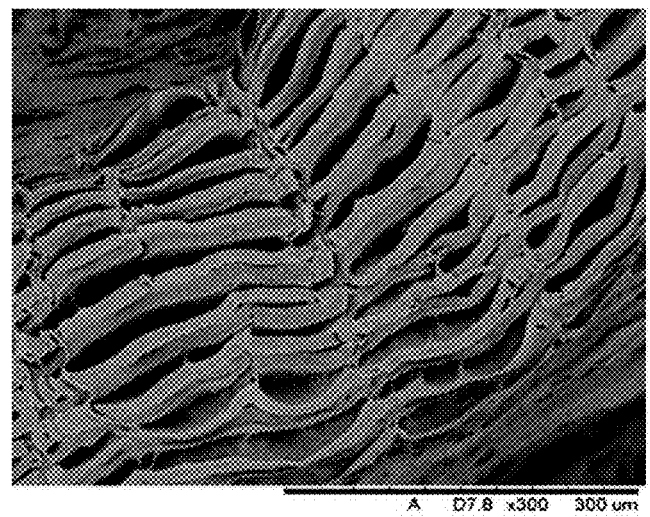
FIG. 25 is SEM micrograph of the fourth stable flake.

The cross-section of the fourth stable flake under SEM measurement is shown in FIG. 25, where the fourth stable flake retains the longitudinal collagen fibers, but the structure of the fourth stable flake is loose and the average ultimate stresses thereof is relatively low (swelling form).

Figure 26:
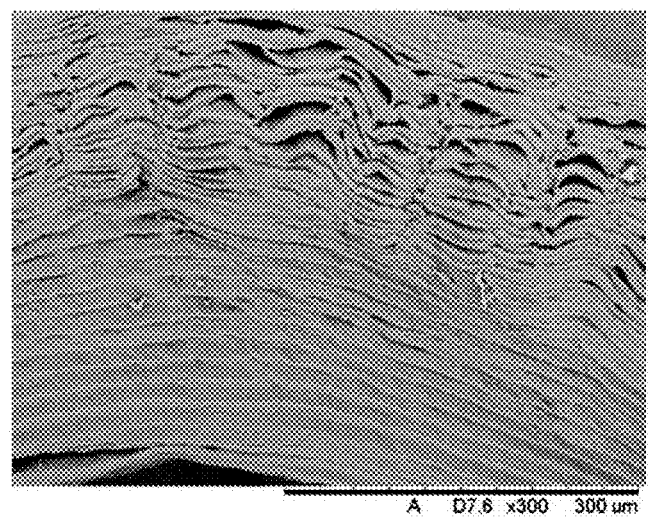
FIG. 26 is SEM micrograph of the fifth stable flake.

The cross-section of the fifth stable flake under SEM measurement is shown in FIG. 26, where the fifth stable flake retains the longitudinal collagen fibers, and the light transmittance of the second stable flake is about 70%.

Figure 27:
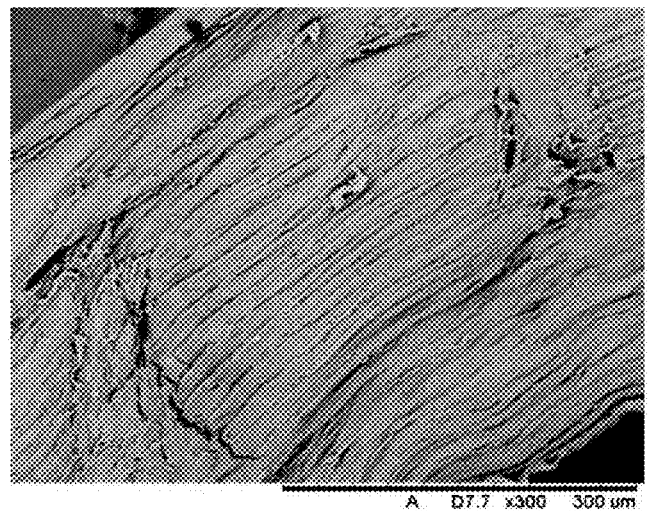
FIG. 27 is SEM micrograph of the sixth stable flake.

The cross-section of the sixth stable flake under SEM measurement is shown in FIG. 27, where although the sixth stable flake lose some longitudinal collagen fibers, the sixth stable flake still has most of the longitudinal collagen fibers. The light transmittance of the sixth stable flake is about 80-85%, and the average ultimate stresses of the sixth stable flake is close to that of the seventh stable flake.

Figure 28:
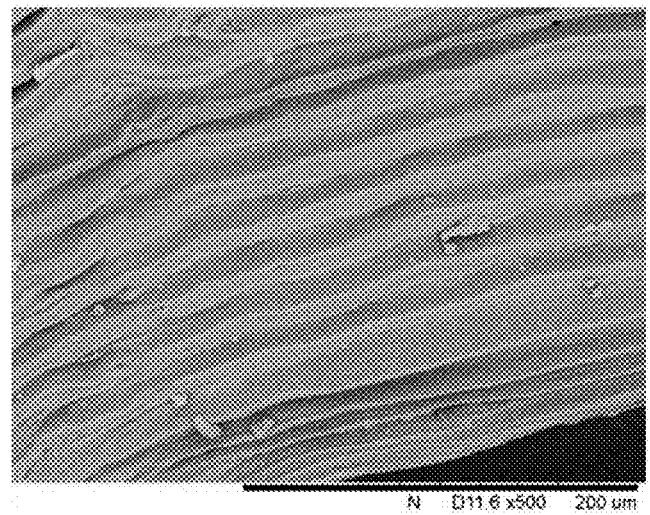
FIG. 28 is SEM micrograph of the seventh stable flake.

The cross-section of the seventh stable flake under SEM measurement is shown in FIG. 28, where although the seventh stable flake lose some longitudinal collagen fibers, and the structure thereof is neatly and closely stacked, the seventh stable flake still has most of the longitudinal collagen fibers. The light transmittance of the seventh stable flake is larger than 90%, and the average ultimate stresses of the seventh stable flake is 2.5-fold larger than that of the fifth stable flake.

Twelfth Experiment: The Different Thickness

In one case, the second shapeable flake is cut by 2 mm clamped tool, and then is treated according to the foregoing fourth embodiment of the stabilizing step, to obtain the optically clear flake in stable state (hereafter referred to as eighth stable flake).

In another case, the second shapeable flake is cut by 5 mm clamped tool, and then is treated according to the foregoing fourth embodiment of the stabilizing step, to obtain the optically clear flake in stable state (hereafter referred to as ninth stable flake).

The thickness of the eighth stable flake is 208±36.8 µm, the light transmittance of the eighth stable flake is larger than or equal to 90%, and the sewability of the eighth stable flake is larger than or equal to 40 g.

The thickness of the ninth stable flake is 500±60.8 µm, and the sewability of the ninth stable flake is larger than or equal to 55 g.

The ratio of the cutting thickness and the final thickness (after stabilizing) is about 1:0.1.

Twelfth Experiment: The Water Content Test

The second shapeable flake is cut, and then is treated according to the foregoing fourth embodiment of the stabilizing step, to obtain the optically clear flake in stable state (hereafter referred to as tenth stable flake).

When the tenth stable flake has the thickness of 200 µm, the water content thereof is about 90%.

Thirteenth Experiment: Cytotoxcity Test

The cytotoxcity test is performed according to ISO10993-12. The material extract is extracted from the seventh stable flake, and then the material extract is added into the culture medium to culture the cells. The tested value of the culture medium with the material extract divided by the tested value of the culture medium without the material extract equals larger than 92%. The result of the cytotoxcity test larger than 70% means pass.

Fourteenth Experiment: The Shaping Procedure, the Stabilization Procedure and the Crosslinking Procedure The second purified fish skin is cut off the fish back portion, the fish belly portion and the fish tail portion where have less collagen and cannot swell better, to retain central rectangular portion of the second purified fish skin. The size of the central rectangular portion is 7*24 cm. The central rectangular portion is re-cut into 8 pieces with the size of 7*3 cm. Herein, the surface of each section originates from the cross-section of the central rectangular portion. Each piece is immersed in a 0.5 L/0.1 M acetic acid solution for 6 hours, and then placed into the ice for 16 hours, to obtain the shapeable flake (hereafter referred to as third shapeable flake).

Next, the third shapeable flake is treated according to the foregoing fourth embodiment of the stabilizing step, to obtain the optically clear flake in stable state (hereafter referred to as eleventh stable flake).

Fifteenth Experiment: The Observation of the Eleventh Stable Flake

When the eleventh stable flake has the thickness of 50 µm to 60 µm, the light transmittance of the eleventh stable flake is larger than or equal to 95%, and the sewability of the eleventh stable flake is larger than or equal to 60 g. When the eleventh stable flake has the thickness of 90 µm to 170 µm, the light transmittance of the eleventh stable flake is larger than or equal to 90%, and the sewability of the eleventh stable flake is larger than or equal to 60 g. When the eleventh stable flake has the thickness of 190 µm to 250 µm, the light transmittance of the eleventh stable flake is larger than or equal to 85%, and the sewability of the eighth stable flake is larger than or equal to 60 g. When the eleventh stable flake has the thickness of 280 µm to 320 µm, the light transmittance of the eleventh stable flake is larger than or equal to 70%, and the sewability of the eleventh stable flake is larger than or equal to 60 g. The largest sewability is larger than 150 g. The average ultimate stresses of the eleventh stable flake is 2-fold larger than that of the seventh stable flake.

Sixteenth Experiment: Preparing a Collagen Solution

The second purified fish skin is immersed in a 0.01 M acetic acid solution for 2 hours, and then removed the impurities, to obtain the shapeable flake. Next, the collagen solution is extracted from this shapeable flake by an extraction procedure.

Seventeenth Experiment: Preparing a Collagen Sponge

The second purified fish skin is immersed in a 0.1 M acetic acid solution for 1 hours, and then lyophilized, to obtain the collagen sponge.

Eighteenth Experiment: Preparing a Collagen Film

The second purified fish skin is immersed in a 0.01 M acetic acid solution for 2 hours, and then removed outer layer, to obtain the shapeable flake. Next, the shapeable flake is re-immersed in a 0.1 M acetic acid solution for 1 hour, to obtain the collagen film. As above, according to the embodiments, the tissue repair material derived from fish skin and manufacturing method thereof is applied to provide the tissue repair material suitable for use as a patch, a cover, a carrier, a scaffold, an implant or a reagent in various tissues. The tissue repair material has collagens to improve the wounded tissue repair, and has particular characters for desired tissue repair application. Furthermore, so far the factors of the terrestrial animal transmitted disease (caused by virus) do not survive on the tissue repair material derived from fish skin.

What is claimed is:

1. A manufacturing method of a tissue repair material derived from fish skin, comprises:
    obtaining a fish skin without a fish flesh;
    removing fish scales, oil, cells, chromatophores and pocket structures from the fish skin to obtain a purified fish skin;
    treating the purified fish skin with acidic solution to obtain a shapeable flake without breakdown; and
    shaping the shapeable fish skin to obtain a shaped flake in a particular form, wherein the shaping step comprises cutting the shapeable flake to obtain the shaped flake, wherein a surface of the shaped flake is a cross section of the shapeable flake.

2. The manufacturing method according to claim 1, further comprising washing the shaped flake with water.

3. The manufacturing method according to claim 2, further comprising dehydrating the shaped flake before the washing step.

4. The manufacturing method according to claim 2, further comprising dehydrating the shaped flake after the washing step.

5. The manufacturing method according to claim 4, further comprising backwatering the shaped flake after the dehydrating steps.

6. The manufacturing method according to claim 5, further comprising dehydrating the shaped flake after the backwatering step.

7. The manufacturing method according to claim 1, further comprising:
    extracting a collagen solution from the shapeable flake.

8. The manufacturing method according to claim 1, further comprising:
    lyophilizing the shapeable flake.

9. The manufacturing method according to claim 1, wherein the treating step comprises:
    treating the purified fish skin with acidic solution more than two times to obtain the shapeable flake without breakdown;
    removing at least one outer layer of the shapeable flake between any two acid-treating steps.

* * * * *